United States Patent
Cormier

(10) Patent No.: US 10,466,211 B2
(45) Date of Patent: Nov. 5, 2019

(54) ROTARY INJECTION VALVE WITH INTERNAL SAMPLE LOAD CHANNEL

(71) Applicant: WATERS TECHNOLOGIES CORPORATION, Milford, MA (US)

(72) Inventor: Sylvain G. Cormier, Mendon, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 0 days.

(21) Appl. No.: 16/084,456

(22) PCT Filed: Mar. 17, 2017

(86) PCT No.: PCT/US2017/022858
§ 371 (c)(1),
(2) Date: Sep. 12, 2018

(87) PCT Pub. No.: WO2017/161216
PCT Pub. Date: Sep. 21, 2017

(65) Prior Publication Data
US 2019/0120799 A1    Apr. 25, 2019

Related U.S. Application Data

(60) Provisional application No. 62/309,538, filed on Mar. 17, 2016.

(51) Int. Cl.
*G01N 30/20* (2006.01)
*F16K 11/085* (2006.01)
(Continued)

(52) U.S. Cl.
CPC ............ *G01N 30/20* (2013.01); *F16K 11/085* (2013.01); *G01N 30/06* (2013.01); *G01N 30/22* (2013.01);
(Continued)

(58) Field of Classification Search
CPC .. G01N 3/20; G01N 3/22; G01N 3/06; G01N 2030/202; G01N 2030/201; G01N 2030/207; F16K 11/085
See application file for complete search history.

(56) References Cited

U.S. PATENT DOCUMENTS 4,068,528 A * 1/1978 Gundelfinger ......... G01N 30/20
73/864.84
4,243,071 A * 1/1981 Shackelford ........... G01N 30/20
137/625.46
(Continued)

FOREIGN PATENT DOCUMENTS

WO    2016089515 A1    6/2016

OTHER PUBLICATIONS

International Search Report & Written Opinion in PCT/US17/22858 dated Jul. 17, 2017; 13 pages.
(Continued)

*Primary Examiner* — Jonathan M Dunlap
(74) *Attorney, Agent, or Firm* — Schmeiser, Olsen & Watts LLP; William G. Guerin

(57) ABSTRACT

A rotary injection valve used in chromatography includes a stator having a stator sealing surface and a sample load channel disposed inside the stator body below the stator sealing surface. The valve can have a reduced number of ports thereby allowing faster integration of the valve into a chromatographic system. Flow restriction is reduced compared to valves that use an external sample loop for a similar volume of sample. The lack of stator ports for the sample load channel eliminates the potential for carryover created by external valve couplings. Another advantage is the reduction of surface wear achieved by locating the sample load channel below the stator sealing surface.

14 Claims, 9 Drawing Sheets

(51) Int. Cl.
*G01N 30/06* (2006.01)
*G01N 30/22* (2006.01)

(52) U.S. Cl.
CPC . *G01N 2030/201* (2013.01); *G01N 2030/202* (2013.01); *G01N 2030/207* (2013.01)

(56) References Cited

U.S. PATENT DOCUMENTS

| | | | | |
|---|---|---|---|---|
| 4,506,558 | A * | 3/1985 | Bakalyar | G01N 30/20 |
| | | | | 73/863.72 |
| 5,010,921 | A * | 4/1991 | Nohl | F16K 11/074 |
| | | | | 137/625.11 |
| 5,207,109 | A * | 5/1993 | Olsen | G01N 30/20 |
| | | | | 73/863.73 |
| 8,196,456 | B2 * | 6/2012 | Hochgraeber | G01N 30/20 |
| | | | | 73/61.55 |
| 9,176,101 | B2 | 11/2015 | Moeller | |
| 2009/0050212 | A1 | 2/2009 | Dourdeville et al. | |
| 2010/0171055 | A1 | 7/2010 | Dourdeville | |
| 2011/0006237 | A1 * | 1/2011 | Tower | F16K 3/08 |
| | | | | 251/304 |
| 2012/0227470 | A1 | 9/2012 | Gerhardt et al. | |
| 2013/0112604 | A1 * | 5/2013 | Keene | F16K 11/0743 |
| | | | | 210/198.2 |
| 2015/0114501 | A1 * | 4/2015 | Tower | F16K 3/08 |
| | | | | 137/625.15 |
| 2016/0054274 | A1 | 2/2016 | Cormier et al. | |
| 2016/0069844 | A1 | 3/2016 | Jackson et al. | |

OTHER PUBLICATIONS

International Preliminary Report on Patentability in PCT/US17/22858 dated Sep. 27, 2018; 10 pages.

* cited by examiner

ROTARY INJECTION VALVE WITH INTERNAL SAMPLE LOAD CHANNEL

RELATED APPLICATION

This application claims the benefit of and priority to U.S. provisional application No. 62/309,538, filed Mar. 17, 2016, titled "Rotary Injection Valve with Internal Sample Load Channel" the entirety of which is incorporated by reference herein.

FIELD OF THE INVENTION

The invention relates generally to an injection loop for a chromatography system. More particularly, the invention relates to an injection loop formed inside the stator of a rotary shear seal valve.

BACKGROUND

Chromatography is a set of techniques for separating a mixture into its constituents. For instance, in a liquid chromatography (LC) application, a solvent delivery system takes in and delivers a mixture of liquid solvents to an autosampler (also called an injection system or sample manager), where an injected sample awaits the arrival of this mobile phase. The mobile phase with the dissolved injected sample passes to a column. By passing the mixture through the column, the various components in the sample separate from each other at different rates and thus elute from the column at different times. A detector receives the separated components from the column and produces an output from which the identity and quantity of the analytes may be determined.

Some LC injection systems use a fixed-volume sample loop coupled to two ports of an injection valve. Sample is loaded by pumping sample from a sample reservoir or other sample source into the sample loop. Subsequently, the valve is reconfigured such that the sample loop is inserted into the mobile phase flow path. A typical injection valve uses a sample loop formed of a length of tubing that is plumbed to two valve ports. Such sample loops work well for large sample volumes, i.e., volumes of approximately 1.0 µL or greater; however, smaller sample injection volumes (e.g., volumes on the order of 0.1 µL or less) are more difficult to accommodate. More specifically, a minimum tubing length is required to connect between the two valve ports. Tubing with a sufficiently small inner diameter for these low sample volumes is difficult to obtain due in part to limitations on the manufacturing tolerance for the inner diameter. Thus two sample loops of the same length and specified inner diameter can vary significantly in terms of the volume capacity of the tubing. In addition, although the required volume is small, the small inner diameter means that a higher pressure is required to load sample into the sample loop.

SUMMARY

In one aspect, the invention features a rotary injection valve having a stator and a rotor. The stator has a stator sealing surface and a plurality of ports including a sample port to receive a flow of a chromatographic sample, a mobile phase port to receive a flow of a mobile phase, a waste port to dispense the flow of the chromatographic sample to waste and a column port to provide the flow of the mobile phase to a chromatographic column. The stator also includes a sample load channel disposed inside the stator body below the stator sealing surface. The sample load channel extends between a first port and a second port in the stator sealing surface. The rotor has a rotor seal surface in contact with and sealing against the stator sealing surface. A plurality of valve channels is disposed on at least one of the stator sealing surface and the rotor seal surface. When the rotary injection valve is in a load configuration, an end of the sample load channel is in fluidic communication with the sample port and the other end of the sample load channel is in fluidic communication with the vent port to thereby enable the chromatographic sample to flow into the sample load channel. When the rotary injection valve is in an inject configuration, one end of the sample load channel is in fluidic communication with the mobile phase port and the other end of the sample load channel is in fluidic communication with the column port to thereby enable the chromatographic sample in the sample load channel to be injected into the flow of the mobile phase.

In some embodiments, the sample load channel includes a horizontal portion below the stator sealing surface, a first vertical portion extending from one end of the horizontal portion to the stator sealing surface and a second vertical portion extending from an opposite end of the horizontal portion to the stator sealing surface.

In another aspect, the invention features a method of fabricating a stator for a rotary injection valve. For a first section of a button body of a stator having a stator sealing surface, a first diffusion bond surface and plurality of fluidic channels each extending between the stator sealing surface and the first diffusion bond surface, and for a second section of the button body of the stator having a second diffusion bond surface and a plurality of fluidic channels extending therefrom, wherein the first and second sections of the button body are separated from each other, the method includes forming a horizontal portion of a sample load channel on one of the first and second diffusion bond surfaces. The first and second sections of the button body are aligned so that the diffusion bond surfaces are in contact with each other and so that each of the vertical channels in the first section is in communication with an end of the horizontal portion of the sample load channel or one of the fluidic channels in the second section. A diffusion bonding process is performed on the aligned first and second sections of the button body to form a button body having a sample load channel inside the button body below the stator sealing surface.

In still another aspect, the invention features a stator for a rotary injection valve. The stator includes a stator button having a stator sealing surface and a plurality of ports on the stator sealing surface including a sample port to receive a flow of a chromatographic sample, a mobile phase port to receive a flow of a mobile phase, a waste port to dispense the flow of the chromatographic sample to waste and a column port to provide the flow of the mobile phase to a chromatographic column. The stator button further includes a sample load channel disposed inside the stator button below the stator sealing surface. The sample load channel has a first vertical portion and a second vertical portion each extending from a first end at a port on the stator sealing surface to a second end below the stator sealing surface. The sample load channel has a horizontal portion that extends between the second ends of the first and second vertical portions.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

DETAILED DESCRIPTION

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to embodiments thereof as shown in the accompanying drawings. It is to be understood that such terms like top, bottom, below, upper, lower, horizontal and vertical are relative terms used for purposes of simplifying the description of features as shown in the figures, and are not used to impose any limitation on the structure or use of any structures or methods described herein. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure.

Figure 1A:
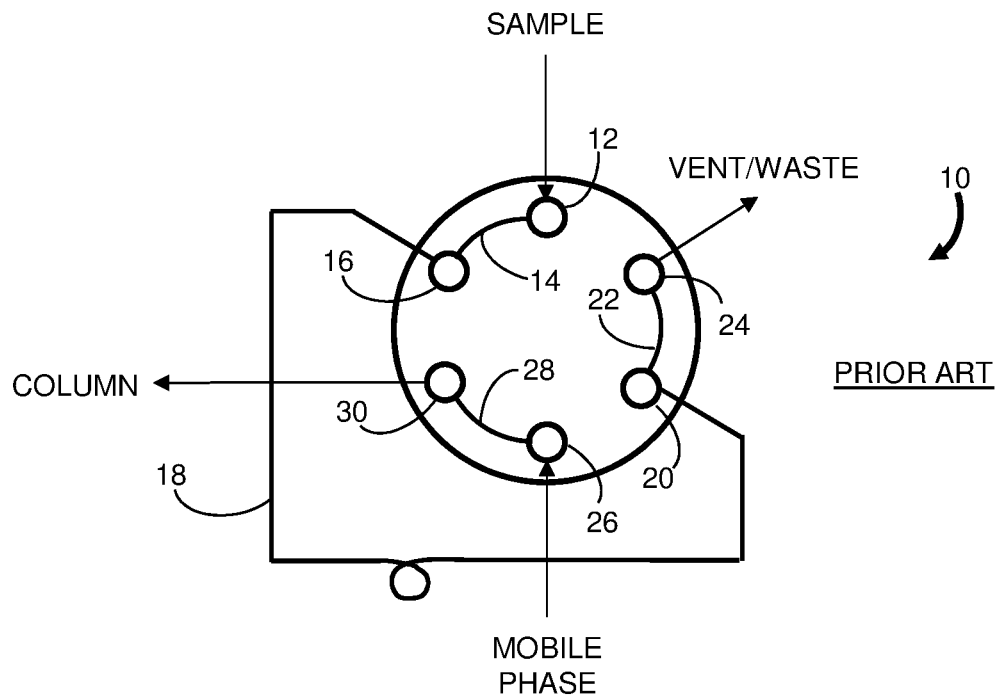
FIG. 1A and FIG. 1B are illustrations of a rotary injection valve in a sample-loading configuration and a sample-injection configuration, respectively.

A rotary shear seal valve is often used as a rotary injection valve in High Performance Liquid Chromatography (HPLC) systems. Typical rotary shear seal valves have two operating configurations: a load configuration, as illustrated by the rotary injection valve 10 in FIG. 1A; and an inject configuration, as illustrated for the same rotary injection valve 10 in FIG. 1B.

In the load configuration, sample enters a sample load port 12 of the valve 10. A first valve channel 14 places the sample load port 12 in fluidic communication with a first sample loop port 16. The sample enters the sample loop 18 which extends from the first sample loop port 16 to second sample loop port 20. A second valve channel 22 places the second sample loop port 20 in fluidic communication with a vent port 24. A mobile phase inlet port 26 is configured to receive a flow of mobile phase. A third valve channel 28 places the mobile phase inlet port 26 in fluidic communication with a column port 30 where the mobile phase exits the valve 10 and flows toward a chromatography column.

Figure 1B:
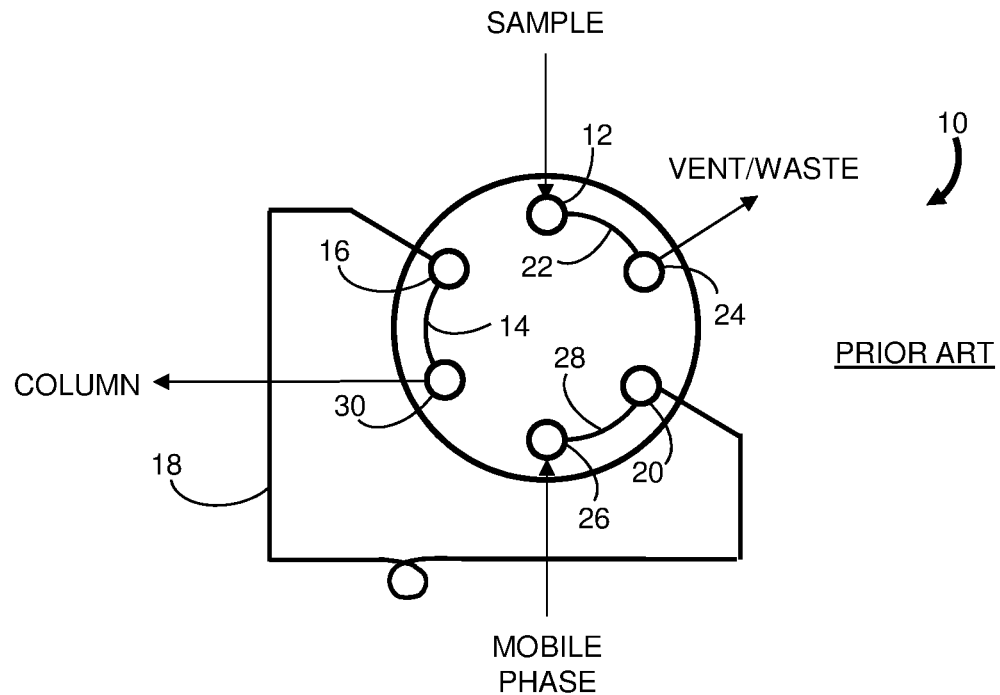

In the inject configuration shown in FIG. 1B, the rotary injection valve 10 is configured so that the first valve channel 14 provides a fluidic communication between the first sample loop port 16 and the column port 30, the second valve channel 22 provides a fluidic communication between the sample load port 12 and vent port 24, and the third valve channel 28 provides a fluidic communication between the mobile phase inlet port 26 and the second sample loop port 20. In this configuration, the mobile phase received at the mobile phase inlet port 26 is directed out through the second sample loop port 20 and into the sample loop 18. Thus the sample previously loaded into the sample loop 18 according to FIG. 1A exits the sample loop 18 at the first sample loop port 16, passes through the first valve channel 14 and then flows out from the column port 30 toward the chromatography column.

The rotary injection valve 10 includes a stator and a rotor. The stator includes a stator sealing surface and ports for coupling to external conduits used to pass fluid to or receive fluid from chromatographic system components. The rotor includes a rotor seal surface that is maintained in high pressure contact with the stator sealing surface. The valve 10 is controlled to achieve a desired rotational orientation of the rotor seal surface with respect to the stator sealing surface.

The valve channels 14, 22 and 28 are typically in the form of grooves formed on the stator sealing surface and may also be provided in the form of one or more grooves on the rotor seal surface. The sample loop 18 is typically provided as tubing that is plumbed to the first and second sample loop ports 16 and 20. The sample loop 18 is generally sufficient for sample volumes of 1.0 µL or greater. Smaller sample injection volumes are difficult to achieve using the sample loop 18 because a minimum tubing length is required to connect the first and second sample loop ports 16 and 20, and because the manufacturing tolerance on the inner diameter of the tubing may not be sufficient to accurately define a sample volume for injection. In addition, a higher pressure is required to load a sample loop having a smaller inner diameter.

Figure 2A:
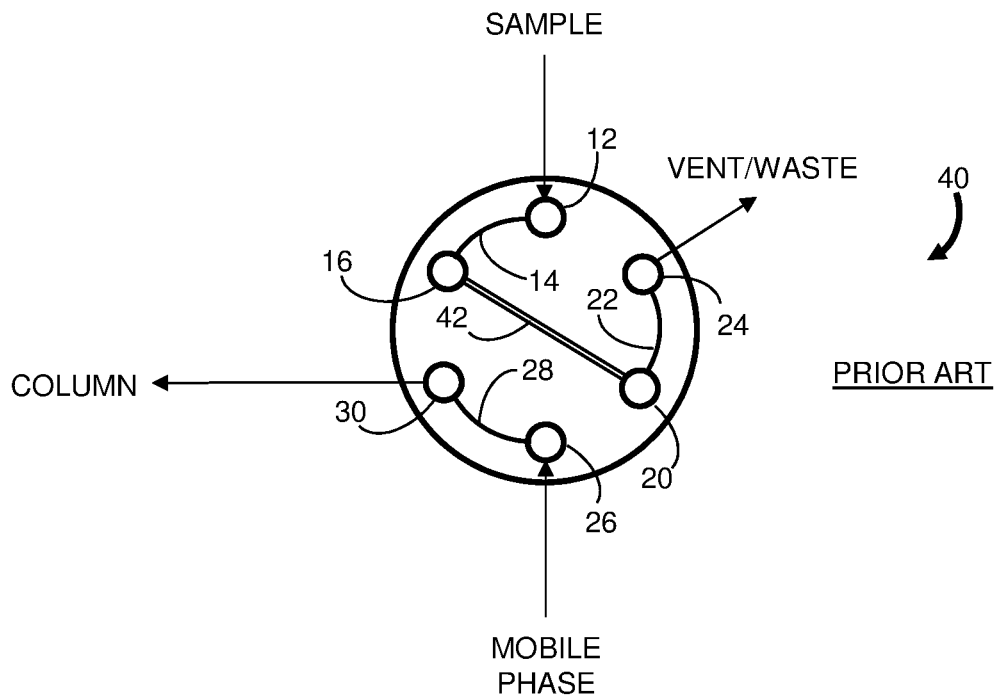
FIG. 2A and FIG. 2B are illustrations of an embodiment of a rotary injection valve having a stator with an internal injection loop and shown in a sample-loading configuration and a sample-injection configuration, respectively.
Figure 2B:
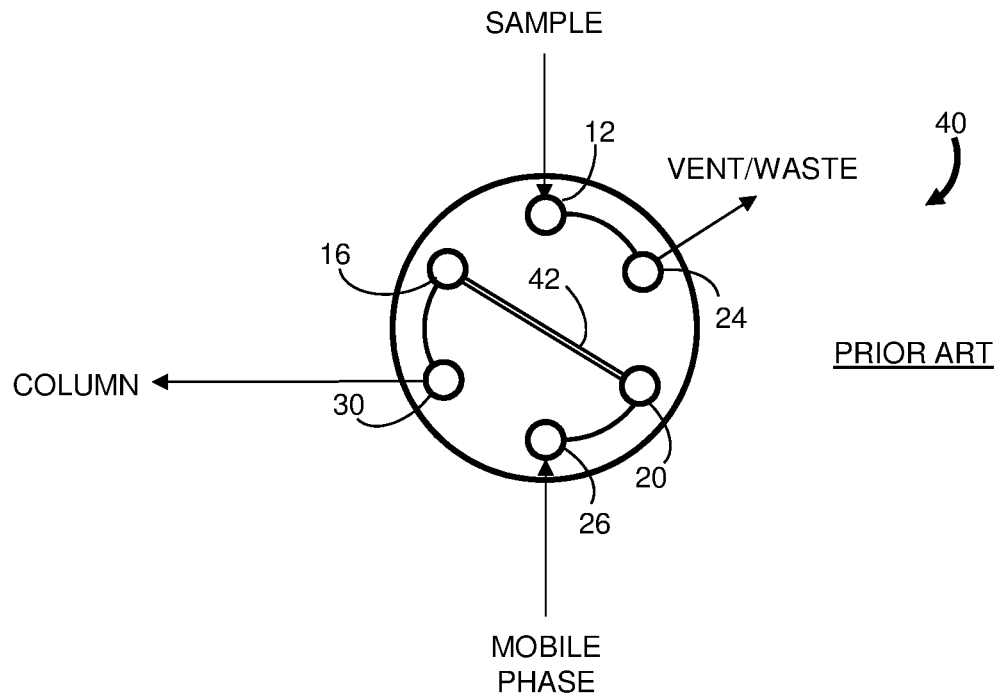

Rotary injection valves having a groove formed directly on the stator sealing surface or the rotor seal surface have been used to provide a small sample volume for injection. An illustration of an example of a rotary injection valve 40 having a groove on a stator sealing surface is shown in a load configuration in FIG. 2A and in an inject configuration in FIG. 2B. The valve 40 can be used at low system pressures, for example at pressures less than 6 Kpsi (40 MPa) such as may be present in a HPLC system. For higher pressure systems, such as ultra performance liquid chromatography (UPLC®) systems where system pressure can be as high as 18 Kpsi (120 MPa) or greater, additional force is required to maintain the stator sealing surface and the rotor seal surface in fluid-tight contact. As a result, the sample loop groove 42 in the stator sealing surface can scrape and damage the rotor seal surface during rotation of the rotor between the valve configuration positions. The damage can occur over a large surface area because the groove 42 is typically arranged along a diameter of the seal surface. Thus this type of rotary injection valve has a reduced lifetime and is often not suitable for high pressure chromatography systems.

Figure 3A:
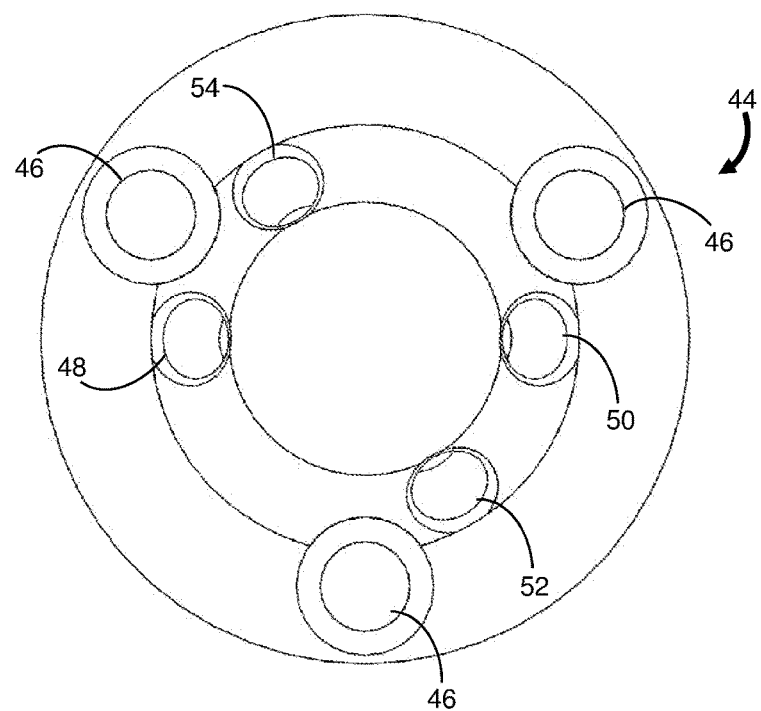
FIG. 3A and FIG. 3B are a top view illustration and a bottom view illustration, respectively, of an embodiment of a stator for a rotary injection valve having an internal sample loop inside a stator button.
Figure 3B:
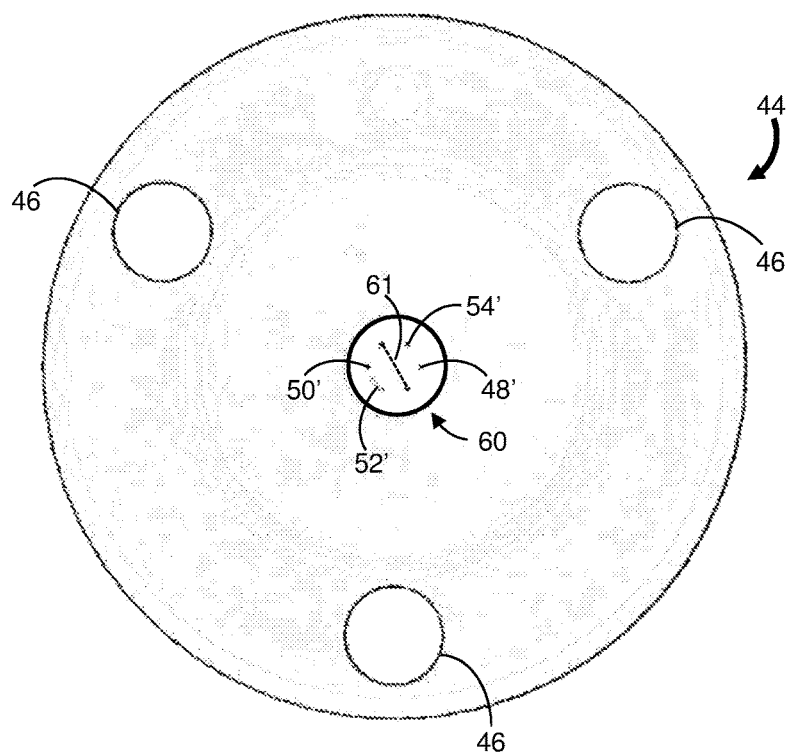

FIG. 3A is a top view of a stator 44 which includes openings 46 to pass bolts or other fasteners used to secure the stator 44 to other structure in the rotary shear seal valve. Four ports are provided in the upper surface to accept fittings for tubing connections. More specifically, ports 48 and 50 permit coupling to tubing form a mobile phase pump and a sample source, respectively. Ports 52 and 54 permit coupling to tubing leading to a waste location and the chromatographic column, respectively. FIG. 3B is a bottom view of the stator 44. A central portion 60, referred to herein as a "button," extends downward from the remainder of the stator body and includes the stator sealing surface that contacts the rotor seal surface. The dashed line 61 depicts a region along the button surface (i.e., the stator sealing surface) below which a sample load channel is disposed. The sample load channel acquires a volume of sample when the rotary injection valve is in a load configuration and dispenses the volume of sample into the mobile phase when the rotary injection valve is in an inject configuration.

Figure 4A:
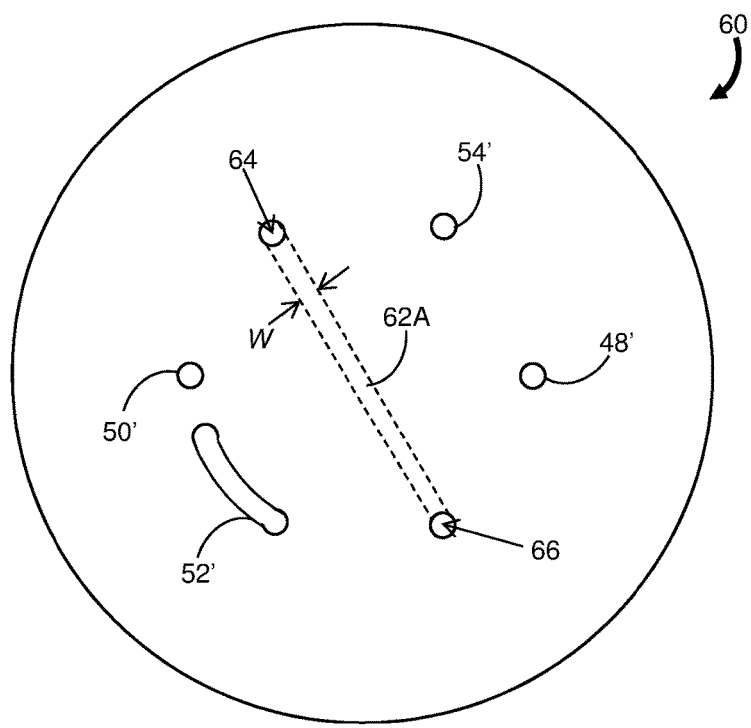
FIG. 4A is a detailed view of the stator sealing surface for the stator of FIG. 3A and FIG. 3B, and shows the location of the internal sample loop with respect to features on the stator sealing surface.

FIG. 4A shows a planar detailed view of the stator sealing surface on the button 60. The four openings, or ports, on the stator sealing surface are designated by primed reference numbers corresponding to the unprimed reference numbers of the counterpart ports on the upper surface shown in FIG. 3A. Parallel dashed lines 62A represent a horizontal portion of a sample load channel 62 that lies below the stator sealing surface and within the body of the button 60. The sample load channel 62 has no direct fluidic pathways through the stator body that lead to a port on the upper surface of the stator.

Figure 4B:
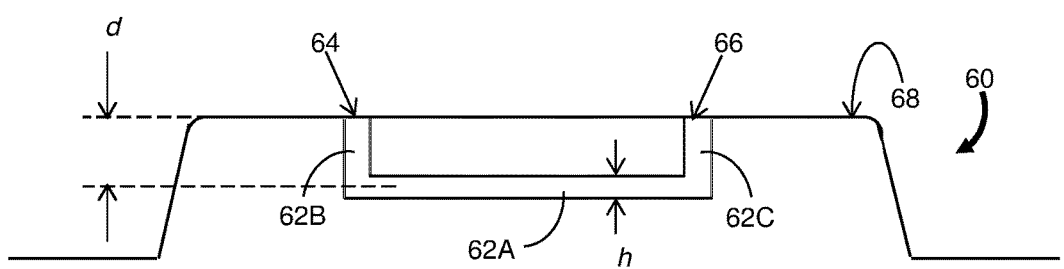
FIG. 4B is a cross-sectional side view of a portion of the stator of FIGS. 3A and 3B showing the location of the internal sample loop within the stator button.

FIG. 4B shows a cross-sectional side view of the button 60 of FIG. 4A where the plane of the figure includes the sample load channel 62. It will be recognized that the sample load channel 62 is configured for a similar purpose to that of the tubing used in an externally coupled sample loop (see sample loop 18 in FIGS. 1A and 1B). In the illustrated embodiment, the sample load channel 62 includes a horizontal channel portion 62A of height h that lies at a depth d below the stator sealing surface 68. By way of a specific numerical example, the height h can be 0.008 in. (200 μm) and the depth d can be 0.010 in. (250 μm). Generally, a horizontal channel portion 62A having a larger height h or cross-sectional area is formed at a greater depth d to support the pressure created by the seal at the stator sealing surface 68. The sample load channel 62 also includes two vertical channel portions 62B and 62C that extend from the ends of the horizontal channel portion 62A upward to ports 64 and 66, respectively, on the stator sealing surface 68. By "embedding" the sample load channel 62 inside the button 60 instead of along the stator sealing surface 68, the channel 62 is prevented from damaging the rotor seal surface during valve operation. The geometrical dimensions of the sample load channel 62 can be defined to achieve a specified sample hold volume. For example, the cross-sectional areas and length of the channel portions can be selected to achieve a particular sample hold volume. It will be recognized that other cross-sectional geometries can also be used. Moreover, the channel portions can have non-linear pathways and the cross-sectional areas of the channel portions can be different. Sample volumes that can be defined by appropriate dimensions for the sample load channel 62 range from less than 1.0 μl to tens of microliters.

Due to manufacturing limitations, it is impractical to machine the horizontal portion of the sample load channel 62 into the body of the button 60; however, the channel 62 can be formed within the body using a method described below based on a diffusion bonding process. The stator fabricated according to this method is the same as if the button 60 portion of the stator were to be sliced horizontally into two sections. The first section includes the stator sealing surface 68 and has a thickness that is approximately the same as the depth d of the horizontal channel portion. The second section includes the remainder of the button body. The channel 62 would then be formed in the newly formed surface in the plane of the slicing on the small disc-shaped portion. Alternatively, the channel 62 would then be formed the newly formed surface of the remainder of the button body at the plane of the slicing.

Figure 5A:
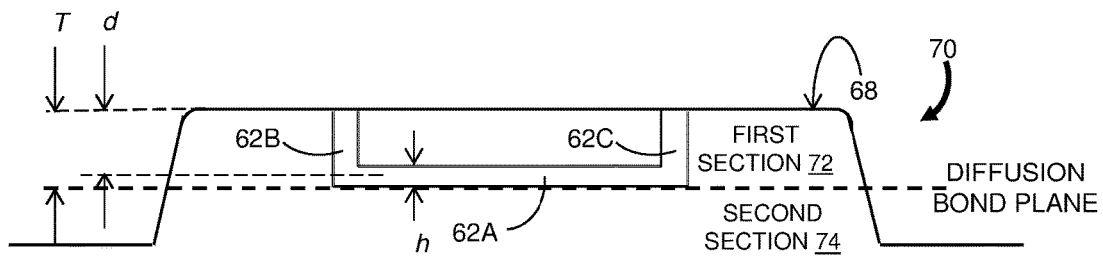
FIG. 5A is a cross-sectional side view of a button for an embodiment of a stator for a rotary injection valve according to the invention.
Figure 5B:
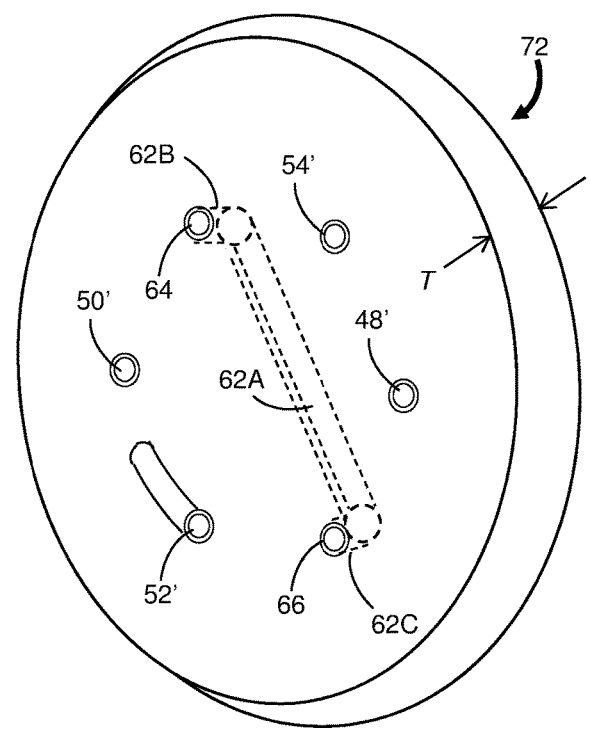
FIG. 5B is a perspective see-through view of a first section of the button of FIG. 5A.
Figure 6:
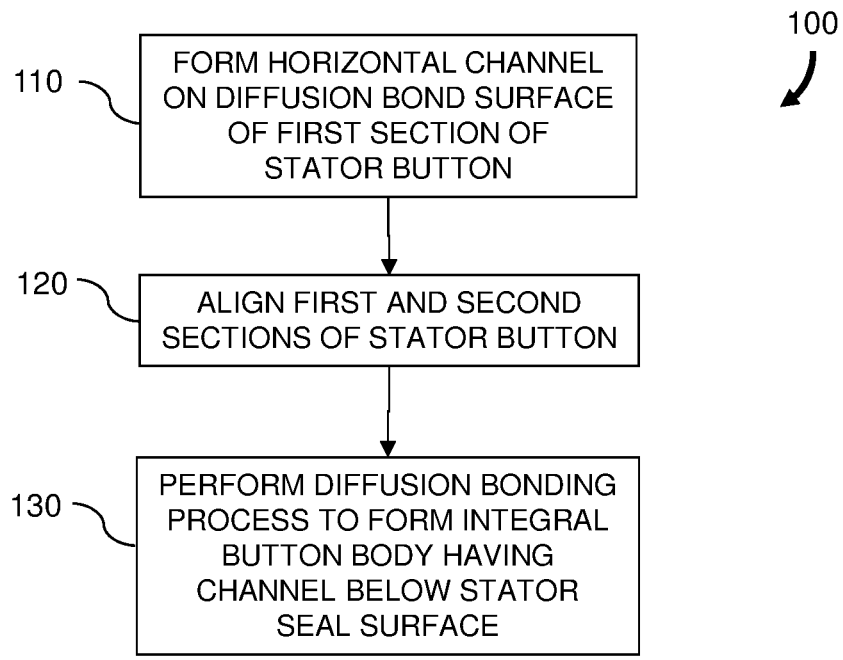
FIG. 6 is a flowchart representation of an embodiment of a method of fabricating a stator for a rotary injection valve.

FIG. 5A is a cross-sectional side view of a button 70 formed according to one embodiment of a method for fabricating a stator for a rotary injection valve. FIG. 5B shows a perspective see-through view of the nominally disc-shaped first section 72 of thickness T where the sample load channel 62 is represented by dashed lines. Reference is also made to FIG. 6 which shows a flowchart representation of an embodiment of a method 100 of fabricating a stator for a rotary injection valve. The method 100 includes forming (110) the horizontal channel portion 62A in a first section 72 of the button 70 on a diffusion bond surface that is opposite to the stator sealing surface 68. The vertical channel portions 62B and 62C are also be formed in the first section 72. Fluidic features of small dimensions (e.g., tens of microns or less) can be formed in the first section 72 using techniques such as chemical etching, electrochemical micromachining, electric discharge machining and the like. In a preferred embodiment, the button sections are formed of titanium. In alternative embodiments, the button sections are formed of stainless steel or MP35N® alloy.

Once all the fluidic channels are formed, the first section is positioned against and aligned (120) to the second section 74 of the button body, that is, the section of the button 70 below the dashed line representing the diffusion bond plane in FIG. 5A. Alignment maintains the proper registration of the channels leading from the ports in the stator sealing surface with the fluid channels leading to the respective counterpart ports on the upper surface of the stator. The first and second sections 72 and 74 are then diffusion bonded (130) to each other to create a single button body having the embedded sample load channel 62. By way of example, a diffusion bonding process suitable for manufacturing the button 70 is disclosed in Patent Publication No. US 20100171055, the entirety of which is incorporated herein by reference. The stator button resulting from the diffusion bonding process can withstand the high fluidic pressures of HPLC systems and UPLC® systems.

Figure 8:
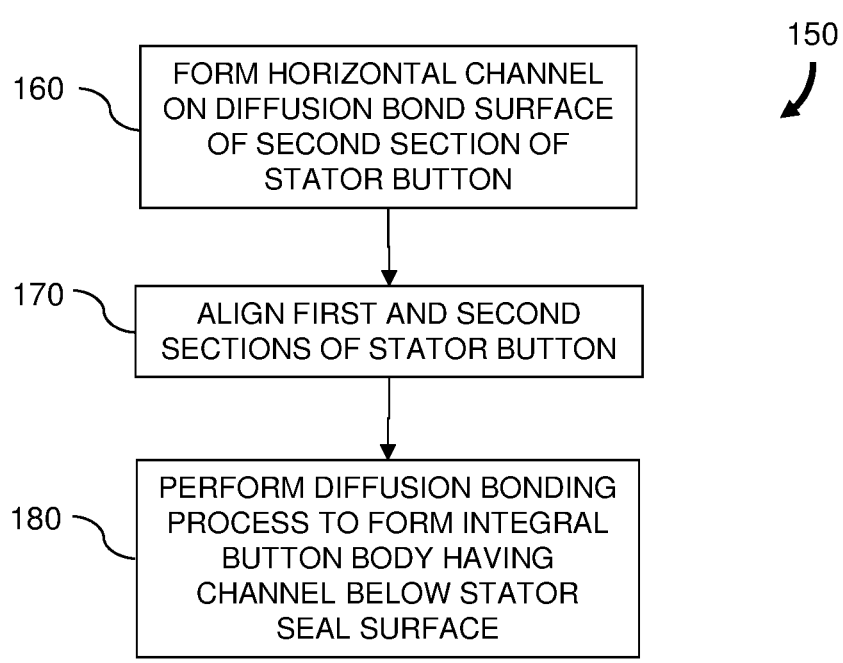
FIG. 8 is a flowchart representation of another embodiment of a method of fabricating a stator for a rotary injection valve.
Figure 7A:
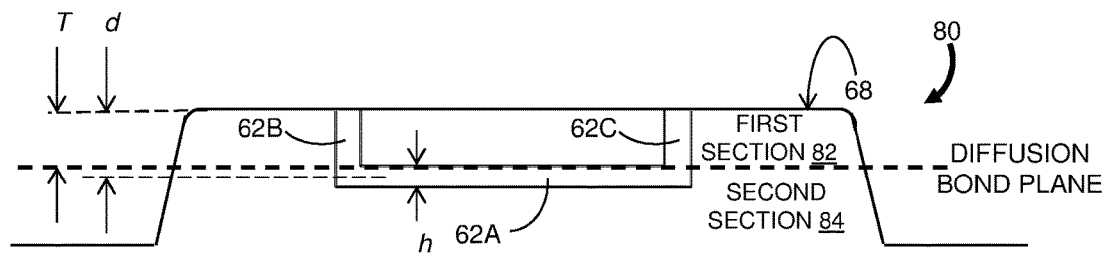
FIG. 7A is a cross-sectional side view of a button for another embodiment of a stator for a rotary injection valve according to the invention.
Figure 7B:
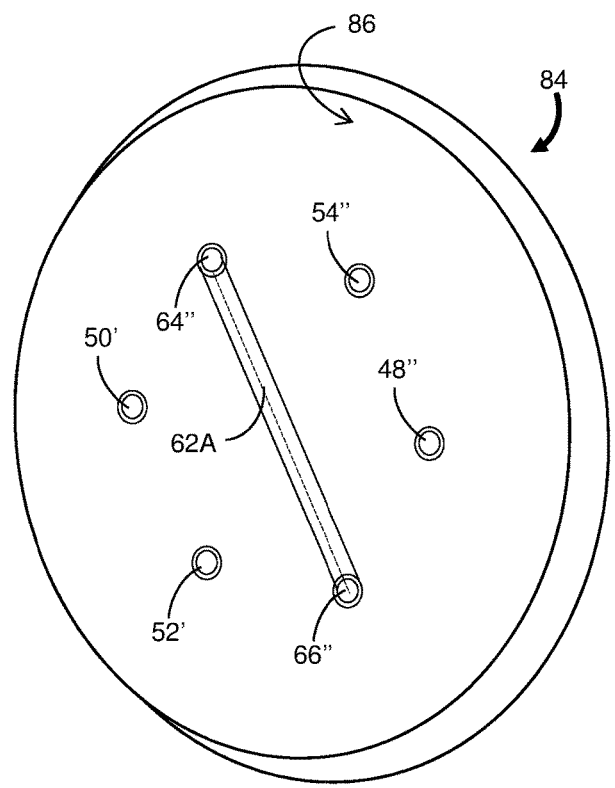
FIG. 7B is a perspective view of a second section of the button of FIG. 7A.

FIG. 7A is a cross-sectional side view of a button 80 formed according to an alternative embodiment of a method for fabricating a stator for a rotary injection valve. FIG. 7B is a perspective view of the second section 84 where the horizontal channel portion 62A is formed along a surface 86 to be diffusion bonded to a surface of the first section 82. Reference is also made to FIG. 8 which shows a flowchart representation of an embodiment of a method 150 of fabricating a stator for a rotary injection valve. The method 150 includes fabricating the horizontal portion 62A of the sample load channel in the second section 84 of the button 80 that is below the diffusion bond plane.

In this alternative embodiment, the vertical channel portions 62B and 62C are formed in the first section 82 of the button 80 along with other vertical channels leading from other ports 48', 50', 52' and 54' on the stator sealing surface 68. The horizontal channel portion 62A is formed (160) on the diffusion bond surface of the second section 84 using any of a variety of processes, for example, chemical etching, electrochemical micromachining, electric discharge machining and the like.

Once all the fluidic channels are formed, the first and second first sections 82 and 84 are positioned with their diffusion bonded surfaces in contact and aligned (170) for proper registration of the fluidic channels. Subsequently, the two sections 82 and 84 are diffusion-bonded to each other to create a single button body.

Figure 9A:
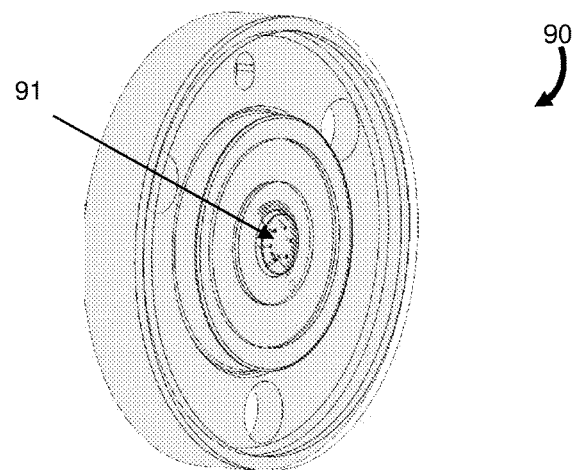
FIG. 9A and FIG. 9B are a perspective view and a bottom view, respectively, of an embodiment of a stator for a rotary injection valve having an internal sample loop.
Figure 9B:
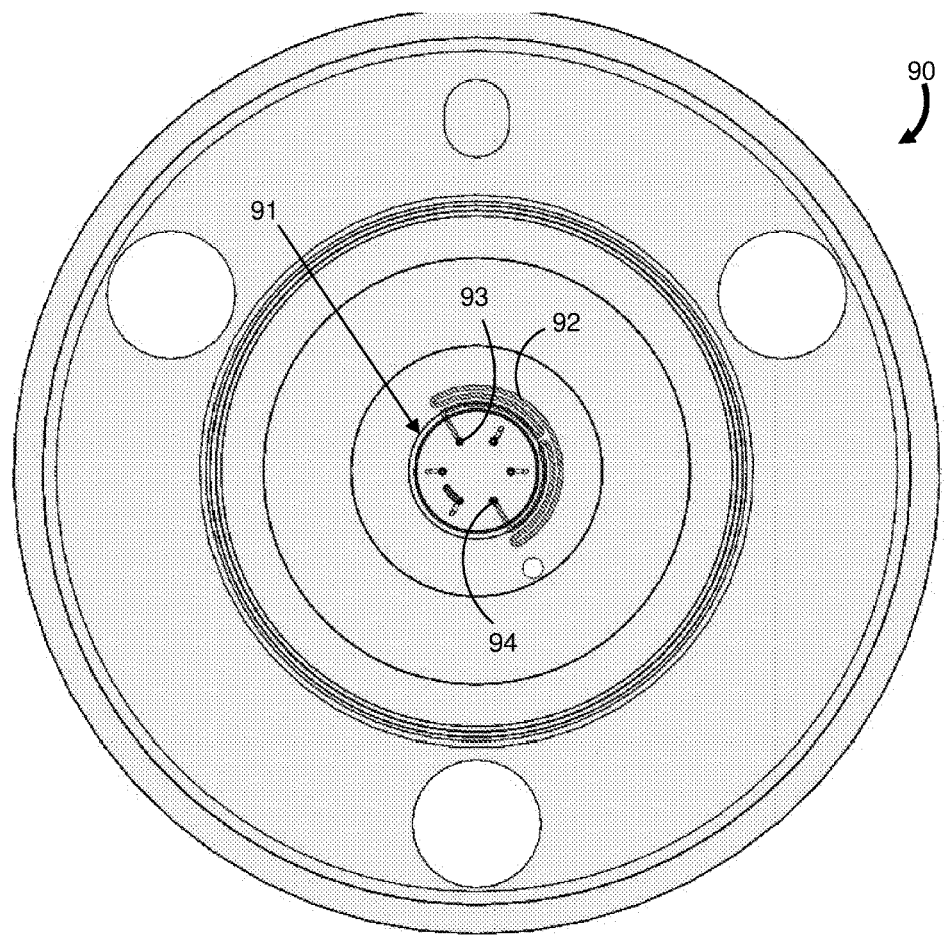

FIGS. 9A and 9B are a perspective view and a bottom view, respectively, of an embodiment of a stator 90 having a button 91 similar to the button 60 shown in FIGS. 4A and 4B except for a sample load channel 92 that extends from a port 93 into the main stator body and back to a second port 94. The sample load channel 92 does not have a linear path to directly couple the ports 93 and 94. Instead, the sample load channel 92 has a non-linear path that includes multiple circumferential path segments along its path to accommodate a greater sample volume.

Figure 10A:
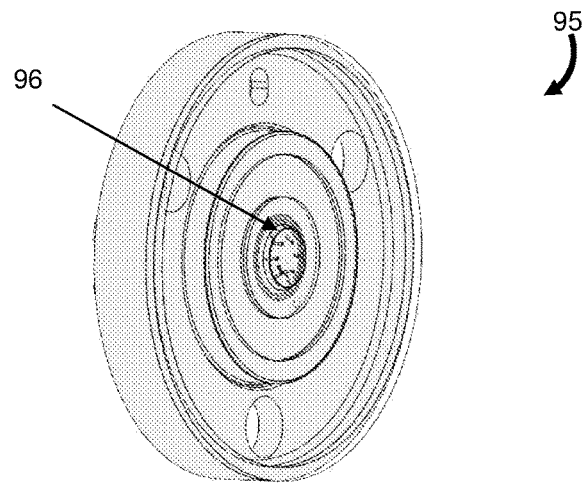
FIG. 10A and FIG. 10B are a perspective view and a bottom view, respectively, of another embodiment of a stator for a rotary injection valve having an internal sample loop.
Figure 10B:
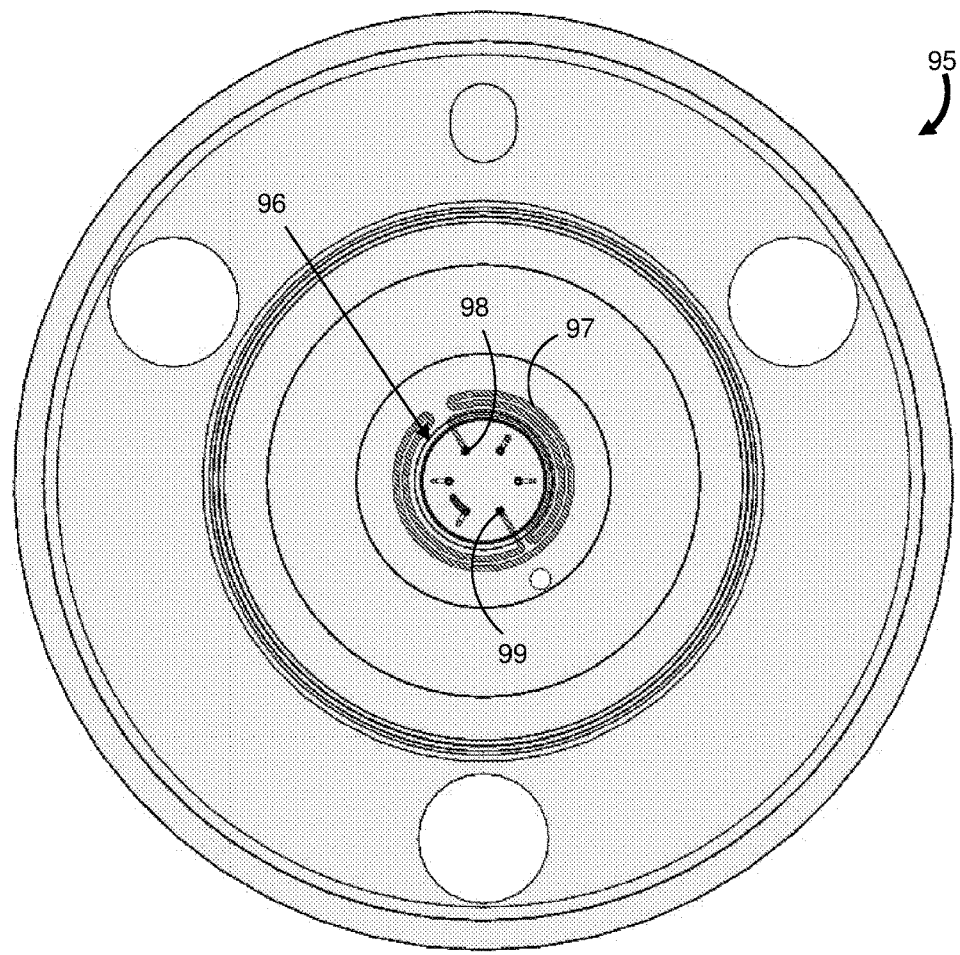

FIGS. 10A and 10B are a perspective view and a bottom view, respectively, of an embodiment of a stator 95 having a button 96 and a sample load channel 97 that extends from a port 98 into the main stator body and back to a second port 99. The sample load channel 97 contains longer circumferential path segments than those of sample load channel 92 in FIG. 9B. The longer circumferential path segments accommodate a greater sample volume. The load channels 92 and 97 are substantially longer than the substantially linear load channel 62 of FIGS. 4A and 4B which has a total length that is only slightly greater than the separation of the ports 64 and 66.

The sample load channels 92 and 97 have accurately defined volumes due to improved inner diameter tolerances available using diffusion bonding processes. Table 1 shows dimensions, tolerances and volumes for various conventional sample loops in which standard tubing has a typical tolerance on the inner diameter of ±0.001 in. (25 µm) and special tubing has an inner diameter tolerance of ±0.001 in. (25 µm).

TABLE 1

| ACQUITY HYPO SAMPLE LOOPS - VOLUME CALCULATIONS | | | | | | | | | |
|---|---|---|---|---|---|---|---|---|---|
| Hypo Sample Loop Size (uL) | Nominal ID (in) | Tolerance+ | Tolerance− | Nominal Length (in) | Tolerance+ | Tolerance− | Nominal Volume (uL) | Minimum Value (uL) | Maxiumum Value (uL) |
| 1 | 0.004 | 0.0005 | 0.0005 | 5.00 | 0.03 | 0.03 | 1.03 | 0.78 | 1.31 |
| 2 | 0.004 | 0.0005 | 0.0005 | 9.75 | 0.03 | 0.03 | 2.01 | 1.53 | 2.55 |
| 5 | 0.007 | 0.0005 | 0.0005 | 7.95 | 0.03 | 0.03 | 5.01 | 4.31 | 5.78 |
| 10 | 0.010 | 0.0005 | 0.0005 | 7.79 | 0.03 | 0.03 | 10.03 | 9.01 | 11.10 |
| ACQUITY SAMPLE LOOPS - VOLUME CALCULATIONS | | | | | | | | | |
| Sample Loop Size (uL) | Nominal ID (in) | Tolerance+ | Tolerance− | Nominal Length (in) | Tolerance+ | Tolerance− | Nominal Volume (uL) | Minimum Value (uL) | Maxiumum Value (uL) |
| 1 | 0.004 | 0.001 | 0.001 | 5.00 | 0.03 | 0.03 | 1.03 | 0.58 | 1.62 |
| 2 | 0.005 | 0.001 | 0.001 | 6.20 | 0.03 | 0.03 | 1.99 | 1.27 | 2.89 |
| 5 | 0.007 | 0.001 | 0.001 | 7.93 | 0.03 | 0.03 | 5.00 | 3.66 | 6.56 |
| 10 | 0.012 | 0.001 | 0.001 | 5.40 | 0.03 | 0.03 | 10.01 | 8.36 | 11.81 |
| 10-Bent | 0.012 | 0.001 | 0.001 | 5.40 | 0.03 | 0.03 | 10.01 | 8.36 | 11.81 |
| 20 | 0.012 | 0.001 | 0.001 | 10.79 | 0.03 | 0.03 | 20.00 | 16.76 | 23.53 |
| 50 | 0.020 | 0.000 | 0.002 | 9.76 | 0.06 | 0.06 | 50.25 | 40.45 | 50.55 |
| 100 | 0.030 | 0.000 | 0.002 | 8.63 | 0.06 | 0.06 | 99.96 | 86.47 | 100.66 |
| 250 | 0.030 | 0.000 | 0.002 | 21.59 | 0.06 | 0.06 | 250.08 | 217.25 | 250.78 |

Table 2 shows dimensions, the improved tolerances and volumes for sample load channels (sample loops) 92 and 97 (and for sample load channels of other embodiments of stators described herein).

TABLE 2

| ACQUITY SAMPLE LOOPS - VOLUME CALCULATIONS | | | | | | | | | |
|---|---|---|---|---|---|---|---|---|---|
| Sample Loop Size (uL) | Nominal ID (in) | Tolerance+ | Tolerance− | Nominal Length (in) | Tolerance+ | Tolerance− | Nominal Volume (uL) | Minimum Value (uL) | Maxiumum Value (uL) |
| 1 | 0.004 | 0.00005 | 0.00005 | 5.00 | 0.03 | 0.03 | 1.03 | 1.00 | 1.06 |
| 2 | 0.005 | 0.00005 | 0.00005 | 6.20 | 0.03 | 0.03 | 1.99 | 1.95 | 2.04 |
| 5 | 0.007 | 0.00005 | 0.00005 | 7.93 | 0.03 | 0.03 | 5.00 | 4.91 | 5.09 |

TABLE 2-continued

ACQUITY SAMPLE LOOPS - VOLUME CALCULATIONS

| Sample Loop Size (uL) | Nominal ID (in) | Tolerance+ | Tolerance− | Nominal Length (in) | Tolerance+ | Tolerance− | Nominal Volume (uL) | Minimum Value (uL) | Maxiumum Value (uL) |
|---|---|---|---|---|---|---|---|---|---|
| 10 | 0.012 | 0.00005 | 0.00005 | 5.40 | 0.03 | 0.03 | 10.01 | 9.87 | 10.15 |
| 10-Bent | 0.012 | 0.00005 | 0.00005 | 5.40 | 0.03 | 0.03 | 10.01 | 9.87 | 10.15 |
| 20 | 0.012 | 0.00005 | 0.00005 | 10.79 | 0.03 | 0.03 | 20.00 | 19.78 | 20.22 |
| 50 | 0.020 | 0.00005 | 0.00005 | 9.76 | 0.06 | 0.06 | 50.25 | 49.69 | 50.81 |
| 100 | 0.030 | 0.00005 | 0.00005 | 8.63 | 0.06 | 0.06 | 99.96 | 98.94 | 100.99 |
| 250 | 0.030 | 0.00005 | 0.00005 | 21.59 | 0.06 | 0.06 | 250.08 | 248.56 | 251.62 |

The volume of a sample load channel is proportional to the square of the channel diameter, therefore the tighter tolerances (e.g., ±0.00005 in. (1.3 μm) inner diameter) for a diffusion-bonded stator sample loop allows for better control of the sample loop volume.

Tables 1 and 2 show that improving the dimensional control of the inner diameter of the sample load channel improves the accuracy from approximately ±40% to approximately ±3% for small volume sample loops (e.g., 1 μL) and from approximately ±15% to approximately ±1% for large volume sample loops (e.g., 100 μL). The effect of improved inner diameter tolerance allows for a reduction in the length of the sample load channel with an increase in the inner diameter. This configuration yields a smaller pressure drop occurs across the sample load channel which results in shorter loading time and lower system pressure. Table 3 shows the advantageous effects of such changes.

prescribed conditions which include, for example, provision of a controlled atmosphere, elevated temperature, compressive stress on a laminate stack, and time. Such conditions generally do not require the use of an intervening filler metal or braze. Vacuum diffusion bonding of titanium and titanium alloys generally provides an integral component, in which grain boundaries of adjoining layers and/or grain boundaries formed at the interface(s) between layers have migrated so as to span the original bond plane or planes. Optionally, a plurality of layers can be bonded at one time within the context of one vacuum-furnace "oven run."

Diffusion bonding of a stacked assembly converts the stack to a bonded state, forming a substantially monolithic structure in which the originally distinct metallic layers are often no longer individually distinguishable. Stated otherwise, an interface between layers (also referred to as a

TABLE 3

ACQUITY SAMPLE LOOPS - VOLUME CALCULATIONS

| Sample Loop Size (uL) | Nominal ID (in) | Tolerance+ | Tolerance− | Nominal Length (in) | Tolerance+ | Tolerance− | Nominal Volume (uL) | Minimum Value (uL) | Maxiumum Value (uL) |
|---|---|---|---|---|---|---|---|---|---|
| 1 | 0.008 | 0.00005 | 0.00005 | 1.22 | 0.001 | 0.001 | 1.0008 | 0.9875 | 1.0142 |
| 2 | 0.008 | 0.00005 | 0.00005 | 2.43 | 0.001 | 0.001 | 2.0016 | 1.9758 | 2.0275 |

In various embodiments described above, a diffusion bonding process is used to create the desired structures. It will be recognized that, prior to the bonding of surfaces, fluid paths for high-pressure titanium-based fluid circuits can be formed using, for example, photochemical through-etching of thin sheets, or photochemical blind-etching of thicker sheets, of the metal material. Alternatively, the material removal required to generate fluid paths may be accomplished by electrochemical milling, laser ablation, laser ablation with oxygen gas feed, electrical discharge machining ("EDM"), focused ion beam ("FIB"), electron-beam cutting, reactive-ion dry etching, mechanical cutting, or any alternate suitable means.

Any suitable diffusion-bonding process can be employed. The diffusion-bonding process may be a solid-state diffusion bonding process in which two nominally flat surfaces are joined at an elevated temperature and applied pressure for a time that may be from a few minutes to several hours. High quality joints may be produced so that neither metallurgical discontinuities nor porosity exist across the bond interface.

Titanium and titanium alloys can be joined, for example, by vacuum diffusion bonding. Some suitable vacuum diffusion-bonding processes are presently utilized in the aerospace industry. Vacuum diffusion bonding permits appropriately-prepared titanium surfaces to be directly bonded under bond-plane) is replaced with a grain structure typical of the bulk material so that the original bond plane is no longer recognizable.

It will be recognized that in alternative embodiments to those described herein the sample load channel may be defined by grooves formed in both the first and second sections of the button. In other embodiments, one or more of the channel portions are nonlinear pathways. In further embodiments, the button body may be formed by diffusion bonding more than two button sections, or layers, into a single button body. For example, the button may include one or more additional fluidic channels having a horizontal portion at a different depth below the stator sealing surface that fluidically couple two or more ports in the stator sealing surface or in the upper surface of the stator. The diffusion bonding of larger numbers of layers enables more complicated fluidic pathways to be formed in the stator button, including fluidic pathways that would otherwise not be possible due to interference of fluidic channels formed in a single plane.

Advantageously, a rotary injection valve fabricated according to the principles described herein requires only four stator ports and the sample volume defined by the dimensions of the sample load channel enables an accurately known small volume of a sample to be acquired and injected into a chromatographic system flow. The reduced number of ports enables quicker integration of the valve into a chromatographic system. Flow restriction is reduced compared to the use of an external sample loop used to hold a similar volume of sample. To change the sample injection volume for a chromatographic system, a stator having a different sample volume along with other valve components that couple to the valve actuator are change, such as the rotor and rotor shaft, are replaced. The lack of stator ports for the sample load channel eliminates the potential for carryover created by external couplings. The location of the sample load channel below the stator sealing surface results in a substantial reduction in surface wear.

While the invention has been shown and described with reference to specific preferred embodiments, it should be understood by those skilled in the art that various changes in form and detail may be made therein without departing from the scope of the invention as defined by the following claims.

The invention claimed is:

1. A rotary injection valve, comprising:
a stator comprising a single stator body having a stator sealing surface and a plurality of ports therein, the ports including a sample port to receive a flow of a chromatographic sample, a mobile phase port to receive a flow of a mobile phase, a waste port to dispense the flow of the chromatographic sample to waste and a column port to provide the flow of the mobile phase to a chromatographic column, the stator body further including a sample load channel disposed inside the stator body below the stator sealing surface, the sample load channel extending between a first port and a second port in the stator sealing surface; and
a rotor having a rotor seal surface in contact with and sealing against the stator sealing surface,
wherein a plurality of valve channels is disposed on at least one of the stator sealing surface and the rotor seal surface and wherein, when the rotary injection valve is in a load configuration, an end of the sample load channel is in fluidic communication with the sample port and another end of the sample load channel is in fluidic communication with the waste port to thereby enable the chromatographic sample to flow into the sample load channel and when the rotary injection valve is in an inject configuration, one of the ends of the sample load channel is in fluidic communication with the mobile phase port and the other of the ends of the sample load channel is in fluidic communication with the column port to thereby enable the chromatographic sample in the sample load channel to be injected into the flow of the mobile phase.

2. The rotary injection valve of claim 1 wherein the stator body and rotor are formed of titanium.

3. The rotary injection valve of claim 1 wherein a horizontal portion of the sample channel is parallel to the sealing surface of the stator.

4. The rotary injection valve of claim 1 wherein a volume of the sample load channel is less than 1.0 microliters.

5. The rotary injection valve of claim 1 wherein the number of ports in the plurality of ports in the stator is four.

6. The rotary injection valve of claim 1 wherein the sample load channel includes a horizontal portion below the stator sealing surface, a first vertical portion extending from one end of the horizontal portion to the stator sealing surface and a second vertical portion extending from an opposite end of the horizontal portion to the stator sealing surface.

7. The rotary injection valve of claim 1 wherein a length of the sample load channel is substantially greater than a distance between any two of the sample port, the mobile phase port, the waste port and the column port.

8. The rotary injection valve of claim 1 wherein the sample load channel is defined by a non-linear path.

9. The rotary injection valve of claim 8 wherein the non-linear path includes at least one circumferential path segment.

10. The rotary injection valve of claim 1 wherein the stator body includes a button that extends from a main stator body and wherein the sample load path is inside the button.

11. The rotary injection valve of claim 10 wherein the stator body includes a button that extends from a main stator body and wherein the sample load path extends from the button through a portion of the main stator body and back to the button.

12. A stator for a rotary injection valve, comprising a stator button having a single button body having a stator sealing surface and a plurality of ports on the stator sealing surface including a sample port to receive a flow of a chromatographic sample, a mobile phase port to receive a flow of a mobile phase, a waste port to dispense the flow of the chromatographic sample to waste and a column port to provide the flow of the mobile phase to a chromatographic column, the single button body further including a sample load channel disposed therein below the stator sealing surface, the sample load channel having a first vertical portion and a second vertical portion each extending from a first end at a port on the stator sealing surface to a second end below the stator sealing surface, the sample load channel having a horizontal portion extending between the second ends of the first and second vertical portions.

13. The stator of claim 12 wherein at least one valve channel is disposed on the stator sealing surface.

14. The stator of claim 12 wherein at least one of the horizontal portion and the first and second vertical portions are nonlinear fluidic pathways.

* * * * *